US005302768A

United States Patent [19]

Hussain

[11] Patent Number: 5,302,768
[45] Date of Patent: Apr. 12, 1994

[54] PROCESS FOR DECARBROMODIPHENYLALKANE PREDOMINANT PRODUCT

[75] Inventor: Saadat Hussain, Baton Rouge, La.

[73] Assignee: Ethyl Corporation, Richmond, Va.

[21] Appl. No.: 844,202

[22] Filed: Mar. 2, 1992

Related U.S. Application Data

[62] Division of Ser. No. 559,655, Jul. 30, 1990.

[51] Int. Cl.[5] .................... C07C 22/04; C07C 25/18
[52] U.S. Cl. .................................. 570/185; 570/184; 252/609
[58] Field of Search ................. 570/184, 185; 568/639

[56] References Cited

U.S. PATENT DOCUMENTS

| | | | |
|---|---|---|---|
| 4,287,373 | 9/1981 | Garman et al. | 568/639 |
| 4,327,227 | 4/1982 | Ayres et al. | 568/639 |
| 4,740,629 | 4/1988 | Brackenridge et al. | 568/639 |
| 4,778,933 | 10/1988 | McKinnie et al. | 568/639 |

FOREIGN PATENT DOCUMENTS 1411524 10/1975 United Kingdom .

Primary Examiner—Robert L. Stoll
Assistant Examiner—Joseph D. Anthony
Attorney, Agent, or Firm—David E. LaRose

[57] ABSTRACT

This invention relates to a process for preparing a white or at least near white product which is predominant in decabromodiphenylalkane, and which contains a minor amount of dodecabromodiphenylalkane.

12 Claims, No Drawings

PROCESS FOR DECARBROMODIPHENYLALKANE PREDOMINANT PRODUCT

This application is a division of application Ser. No. 07/559,655, filed Jul. 30, 1990, now pending.

BACKGROUND

This invention relates to a process for preparing a flame retardant product predominant in decabromodiphenylalkane and containing a minor amount of dodecabromodiphenylalkane.

Polybromodiphenyl alkanes, e.g. decabromodiphenylethane, are known flame retardants for use in polyolefin and polystyrenic-based formulations. On a commercial basis, the polybromodiphenylalkane would be supplied to the formulation as a product predominant in the polybromodiphenylalkane selected. The product would have a form and an impurity content which would be characteristic of the process used to produce it. If the product's physical characteristics, e.g. thermal stability, limit the formulation's processability, then the processor's desire for the product is limited at best. If the product's color is not white or at least near white, the product will be suitable for use in some formulations, however, the product's use may not be acceptable in formulations calling for a white or light color.

The amount of product used in a formulation is a function of the bromine content of the product. Generally, the higher the bromine content in the formulation, the greater the degree of flame retardancy, thermal stability, and/or UV stability of the formulation. However, for any given bromine content in a formulation, formulations containing brominated aliphatic flame retardant products are somewhat less thermally and/or UV stable than formulations utilizing flame retardant products consisting essentially of brominated aromatic compounds.

THE INVENTION

The process of this invention yields a white or near white product which is predominant in decabromodiphenylalkane and contains a minor amount of dodecabromodiphenylalkane. The process comprises: forming a stirrable reaction mass by feeding molten diphenylalkane to a reaction vessel to which a bromination catalyst and bromine had been previously charged, the molten diphenylalkane being maintained under a non-oxidizing atmosphere prior to the feeding, and the bromine (i) containing about 10 ppm or less impurities, and (ii) being charged in an amount which provides from about 15 to about 30 moles of bromine per mole of diphenylalkane fed; maintaining the reaction mass at a temperature in the range of from about 15° C. to about reflux during the feeding; subsequent to the feeding, separating from the reaction mass the decabromodiphenylalkane predominant product as a wet cake; and heat treating the wet cake containing the separated product for a period of time and at a temperature which are sufficient to form the decabromodiphenylalkane predominant product containing the minor amount of dodecabromodiphenylalkane.

Brominated aromatic flame retardant products containing brominated alkylene linkages are expected to adversely effect the physical properties of macromolecular formulations containing such flame retardants. Such effects of the flame retardant in the formulation are evidenced by loss of UV and/or thermal stability of test plaques made from the formulation. Quite surprisingly and unexpectedly, macromolecular formulations containing the flame retardant product of this invention, had excellent physical characteristics.

When preparing the decabromodiphenylalkane of this invention, the diphenylalkane reactant can be represented by the formula:

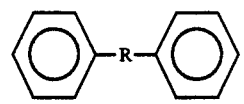

wherein R is an alkylene group containing 1 to 10 carbon atoms. Preferred R groups are methylene and ethylene which give, respectively, the preferred reactants, diphenylmethane and 1,2-diphenylethane. Exemplary of other diphenylalkanes are: 1-methyl-1,2-diphenylethane, 1,4-diphenylbutane, 1,6-diphenylhexane, 2,3-dimethyl-1,4-diphenylbutane, 2-ethyl-3-methyl-1,4-diphenylbutane, 2-methyl-1,7-diphenylhexane, 1,9-diphenylnonane and 1,10-diphenyldecane. The diphenylalkane reactant can be produced by various routes. For example, CA 97 38651d (Japanese Kokai 82/45114) and CA 46 7084g disclose the reaction of benzene and ethylene dihalide in the presence of aluminum trichloride to yield diphenylalkane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often give the final decabromodiphenylalkane product an off color. Exemplary of these color-causing impurities are benzene, toluene, ethylbenzene, diphenylmethane, the methyl and ethyl derivatives of 1,2-diphenylethane, and the like. Diminishing the impurity content can be accomplished in a conventional manner, for example, the diphenylalkane can be recrystallized.

The diphenylalkane is fed to the reaction vessel in a molten state. Thus, the diphenylalkane is at a temperature above its melting point but not so high that it experiences degradation. For diphenylethane, the melting point is about 53° C. to 55° C. and, hence, the diphenylethane is preferably fed at a temperature of from about 55° to about 80° C. The higher temperatures are preferred as the viscosity of the molten diphenylethane can be lower thus making its feed to the reaction vessel more convenient. Most preferred is a temperature within the range of from about 70° C. to about 80° C.

It is most desirable to provide a non-oxidizing atmosphere for the diphenylalkane until it is fed into the reaction vessel. Such an atmosphere can be provided by most inert gases. For example, nitrogen, argon, neon, helium, krypton, xenon, and the like. By providing the inert atmosphere, it has been found that the color characteristics of the product are benefitted.

It has also been found that the bromine utilized in the process of this invention should contain 10 ppm or less organic impurities, e.g. oil, grease, carbonyl containing hydrocarbons, iron and the like, so that there is little, if any, impact on the color attributes of the product. Commercial grade bromine having such purity may be available. If such is not available, the organic impurities and water content of the bromine can be conveniently reduced by mixing together a 3 to 1 volume ratio of bromine and concentrated (94-98 percent) sulfuric acid. A two phase mix is formed which is stirred for 10-16 hours. After stirring and settling,.the sulfuric acid phase, along with the impurities and water, is separated from the bromine phase. To further enhance the purity of the bromine, the recovered bromine phase can be subjected to distillation.

The bromination catalyst used in the process of this invention is preferably $AlCl_3$ and/or $AlBr_3$, although use may be made of aluminum powder, iron powder, $FeCl_3$, and $FeBr_3$, alone or in combination with the aluminum trihalide(s). Other bromination catalysts are suitable, provided that they have sufficient catalytic activity to provide for the extent of bromination called for under the process conditions which will be encountered. Catalytic quantities are used. Typically, the catalysts will be present in an amount within the range of about 0.1 to about 20 weight percent, based on the weight of the diphenylalkane reactant used in the process. A preferred amount is within the range of from about 8 to about 15 weight percent on the same basis, with from about 9.0 to about 11.0 weight percent being most preferred.

The bromination catalyst and bromine can be charged to the reaction vessel in any order or together. It is preferred that both be cooled or heated, as the case may be, prior to their charging so that they will form a mix which is at least near the temperature at which the reaction mass will be maintained during the diphenylalkane addition. While the foregoing is a preferred technique, it is possible, though maybe not as convenient, for the catalyst and bromine, prior to charging, to be at temperatures other than the diphenylalkane addition temperature. If, prior to charging, the catalyst and bromine temperatures are above the addition temperature, the temperature of the resultant mix in the reaction vessel can be lowered to obtain the desired addition temperature. However, care should be taken not to aspirate atmospheric moisture into the reaction vessel during such lowering. The presence of moisture in the reaction vessel is detrimental as many bromination catalysts are deactivated by contact with water.

The amount of elemental bromine ($Br_2$) charged to the reaction vessel should provide sufficient bromine to effect the degree of bromination sought and to provide an easily stirred reaction mass. Generally, from about 15 to about 30 moles of bromine per mole of diphenylalkane feed will be suitable. Preferably from about 17 to about 25 moles of bromine per mole of diphenylalkane are used. A most preferred amount is in the range of from about 18 to about 23 moles of bromine per mole of diphenylalkane. After the reaction is complete, the bromine not used in the ar-substitution will be a liquid component of the reaction mass and will continue to serve the before-mentioned purpose of providing a stirrable reaction mass.

The diphenylalkane addition generally occurs over a period of time and the addition rate is dependent upon the scale of the reaction and the ability to control the temperature and to handle hydrogen bromide evolution. On a commercial scale, the addition could involve about 1.0 to about 10.0 hours or longer.

During the diphenylalkane addition, the reaction mass temperature is kept below about 60° C., and preferably within the range of from 15° to 58° C. Since the bromination of diphenyl alkane is exothermic, cooling of the reaction mass during the diphenylalkane feed will be needed to obtain the addition temperature as required above. The heat of reaction can be removed from the reaction mass by cooling the reaction vessel or by having the reaction mass under reflux conditions so that heat can be removed by the use of an overhead condenser. The rate of diphenylalkane addition will be dependent upon the ability of the equipment to maintain the selected addition temperature.

The bromination reaction can be accomplished at a pressure ranging from subatmospheric to superatmospheric. While the selected pressure is not critical to the invention, from a standpoint of ease of operation, it is desirable to utilize a pressure slightly above atmospheric pressure. Preferably, the pressure is above about 19 psia and most preferably, the pressure is in a range of from about 20 to about 30 psia.

It has been found that the bromination reaction is quite rapid when the diphenylalkane to be brominated is 1,2-diphenylethane. Hence, after completion of the addition of diphenylethane reactant to the reaction mass, there is little need to maintain a ride time at a temperature near or above the reaction temperature to assure substantially complete ar-bromination of the diphenylethane reactant. It may however, be desirable to maintain a post feed ride time at an elevated temperature for the ar-bromination of other diphenylalkane reactants. When a post feed ride time is desired, the reaction mass is brought to a temperature within the range of from about 55° C. to reflux after the addition of the diphenylalkane reactant is complete.

After the post feed ride time, or in the case of diphenylethane, shortly after completion of the addition of diphenylethane, e.g. after about 2 or 3 minutes, the average bromine number of the ar-brominated diphenylalkane is generally at least about 9.0. The average bromine number is defined as the average number of bromine atoms ar-substituted on each brominated diphenylalkane molecule in the product. Thus, an average bromine number of 9.0 indicates that not all of the diphenylalkane molecules in the product have been ring perbrominated, hence, the presence of the lower bromo homologs, e.g. nonobromodiphenylalkane, octabromodiphenylalkane, etc., in the product. As the average bromine number approaches 10.0, the amount of these lower bromo homologs will decrease and the amount of the decabromohomolog will increase.

After substantial completion of the addition of the diphenylalkane reactant, the reaction mass will comprise a liquid-solid mixture. The solid comprises brominated diphenylalkane, catalyst, entrained bromine and other impurities. The liquid will comprise mostly bromine. The brominated diphenylalkane can be separated from the product by steam stripping to remove the non-entrained bromine from the reaction mass and to deactivate the catalyst. The remaining solids are then washed with an aqueous base, e.g. an aqueous solution of NaOH or $Na_2CO_3$, to neutralize and remove any HBr present. A final water washing step is used to obtain a product which is predominant, i.e. 50+ weight percent, in decabromodiphenylalkane. This product is of good color and is further treated to have superior color. A preferred product is one which contains 85+ weight percent, and most preferably 90+ weight percent, decabromodiphenylalkane.

A key feature of this invention is the heat treating step which is performed subsequent to separation of the decabromodiphenylalkane product from the reaction mass. Heat treating the product provides a product with less than about 200 ppm free bromine in the product. This heat treatment step may be performed before or after the product is dried and/or the particle size of the product reduced if desired. During the heat treatment step, the product is maintained at a temperature and for a period of time which are sufficient to form the decabromodiphenylalkane predominant product containing a minor amount of dodecabromodiphenylalkane. By a minor amount is meant less than about 20 weight percent based upon the total amount of dried and treated product thus obtained. Preferably the amount of dodecabromodiphenylalkane is in a range of from about 0.1 weight percent to about 10 weight percent and most preferably in the range of from about 0.4 weight percent to about 8 weight percent.

The heat treatment is performed at a temperature in the range of from about 150° C. to about 400° C. Preferably, the temperature is in a range of from about 180° C. to about 250° C. and most preferably from about 185° C. to about 230° C. The product is maintained at this temperature for 30 minutes or longer depending on the heater design and the temperature for the heat treatment step. Generally, the temperature is maintained for 5 to 8 hours or longer in order to obtain the desired product with less than about 200 ppm free bromine.

While not desiring to be bound by theory, it is believed that the bromine in the decabromodiphenylalkane molecule is retained in the molecule in the form of a complex with the ar-brominated diphenylalkane. Due to this complex, it has been found that drying and grinding procedures generally applicable to ar-brominated diphenyloxide products for removal of entrained bromine, are less successful when applied to decabromodiphenyl alkane for removal of entrained bromine. Instead of removal of the entrained bromine in the decabromodiphenylalkane molecule, at least a portion of the bromine during the heat treating step reacts with the alkylene bridge to form dodecabromodiphenylalkane. When the decabromodiphenylalkane product is decabromodiphenylethane, a minor amount of 1,2-dibromo-bis-pentabromophenylethane is formed.

The decabromodiphenylalkane product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber, and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to those skilled in the art that for all cases no single precise value for the proportion of the product in the formulation can be given, since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 weight percent, preferably 10 to 30 percent, of the product when it is the only flame retardant compound in the formulation.

It is especially advantageous to use the product with an inorganic compound, especially ferric oxide, zinc oxide, zinc borate, the oxide of a-Group V element, for example, bismuth, arsenic, phosphorus and especially antimony, in the formulation. Of these compounds, antimony oxides is especially preferred. If such a compound is present in the formulation, the quantity of product needed to achieve a given flame-retardancy is accordingly reduced. Generally, the product and the inorganic compound are in a weight ratio of from about 1:1 to about 7:1; and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidants, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

The following Examples merely illustrate the invention described herein and are not to be taken as limiting such inventions.

EXAMPLE 1

A 5000 gallon glass-lined reactor was equipped with a mechanical stirrer, a reflux condenser, a temperature sensor, a dip pipe addition line, and a caustic scrubber. The reactor was charged with bromine (33,313 pounds, 208.4 moles) and anhydrous aluminum chloride (175 pounds, 1.31 moles). The reactor was then heated to about 54° C. and molten diphenylethane (DPE) (1,636 pounds, 8.98 moles, 99.3 weight percent DPE) was added through a dip-tube to the reactor contents. The addition of DPE took about 4 hours. During the addition, the pressure in the reaction vessel was maintained at about 5 psig and the reactor was cooled so as to maintain a temperature of about 56° C. A sample taken 14 minutes after completion of the DPE feed was 98.99 weight percent decabromodiphenylethane by gas chromatography analysis (GC) for a 91.5 percent overall yield.

After the DPE feed was complete, the reactor contents were transferred to a stripper vessel containing 900 gallons of water. The stripper vessel contents were then heated with steam until the temperature was about 98° C. and the excess bromine was distilled from the product and condensed. Free water was allowed to drain back to the stripper vessel resulting in aqueous slurry of decabromodiphenylethane predominant product and water. After bromine removal, stripper vessel contents were cooled and 215 gallons of 25 percent caustic (2.01 percent excess) were added. The stripper vessel contents were pumped to a slurry tank and from the slurry tank, pumped batchwise to the centrifuge where the solid decabromodiphenylethane predominant product was recovered as a wet cake. The wet cake was washed with fresh water until the centrate was at a pH of about 8.0 and the wet cake was then ground and dried in a Raymond mill dryer/grinder. Analysis of the dried product indicated about 6000 ppm free bromine, a melting point range of about 346° to 359° C., and Hunter color values of L=83.2-84.2, YI=42.0-45.6, a=2.-51-3.03 and b=18.8-20.1. This dried product was heat treated in a double-cone, tumble dryer at 230° C. for 40 hours. The heat treated product had a melting point of 349° C. and Hunter color values of L=80.4, a=0.5, b=7.5 and Y.I=17.2. GC analysis of the heat treated product indicated about 5.2 weight percent 1,2-dibromo-bis-pentabromophenylethane and 94.8 weight percent decabromodiphenylethane.

EXAMPLE 2

The following example illustrates a method for purifying diphenylethane.

A 1-L beaker was charged with methanol (300 mL). Crude diphenylethane (300 g) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5 g (91.5 percent). The recrystallized material had a melting point of 50° to 54° C. which is slightly higher than the 49°-50° C. for the original starting diphenylethane. The starting diphenylethane had a Y.I. of 33.2 (L=81.2, a=2.9, b=16.1) while the recrystallized diphenylethane material had a Y.I. of 2.8. (L=90.8, a=0.4, b=1.4). The recrystallized product was 99.3 weight percent diphenylethane, 13 ppm benzene, <10 ppm ethyl benzene, and 0.29 weight percent impurities.

The following examples are given to illustrate the properties of formulations containing the product of this invention.

EXAMPLE 3

Four macromolecular formulations were prepared using a Brabender mixer. Formulation A contained 100 percent Cycolac T-1000, an ABS resin sold by Borg-Warner Corporation (now General Electric Company). Formulation B, for comparison purposes contained 78 percent ABS resin sold by Dow Chemical Company, 18 weight percent octobromodiphenyloxide as a flame retardant, and 4 weight percent $Sb_2O_3$. Formulation C contained 78 weight percent ABS resin sold by Dow Chemical Company, 4 weight percent $Sb_2O_3$ and 18 weight percent of the flame retardant product of this invention which flame retardant product contained 5.2 weight percent 1,2-dibromo-bis-pentabromophenylethane. Formulation D contained 84 weight percent high impact polystyrene resin (HIPS from Dow Chemical Company), 4 weight percent $Sb_2O_3$ and 12 weight percent of the flame retardant product of this invention which flame retardant product also contained 5.2 weight percent 1,2-dibromo-bis-pentabromophenylethane. Each formulation was extruded at 175°-215° C. and then injection molded at a temperature ranging from about 200°-215° C. at the inlet to about 225°-240° C. at the outlet and at a molding pressure of 1800 pounds per square inch to form test specimens which are identified in Table I in accordance with the formulation used to product each specimen.

TABLE I

| FORMULATION | A | B | C | D |
|---|---|---|---|---|
| TEST SPECIMEN | 1 | 2 | 3 | 4 |
| PHYSICAL PROPERTIES | | | | |
| Tensile Yield × $10^3$ | 6.5 | 6.1 | 5.6 | 3.7 |
| Tensile Modulus psi × $10^5$ | 4.7 | 3.5 | 3.5 | 3.3 |
| Elongation % | 2.4 | 2.6 | 2.2 | 1.3 |
| Flexural Strength × $10^4$ | 1.0 | 1.0 | 0.98 | 0.62 |
| Flexural Modules psi × $10^5$ | 3.2 | 3.3 | 3.3 | 3.0 |
| UL-94 | | | | |
| $\frac{1}{8}$" | Burn | V-0 | V-0 | V-0 |
| 1/16" | Burn | V-2 | V-0 | V-0 |
| LOI | 19 | 31.6 | 31.6 | 28.0 |
| Heat Deflection °C. $\frac{1}{8}$"/264 psi | 83 | 84 | 89 | 85.5 |
| Melt Index g/10 min (230° C./3800 g) | 6.7 | 6.2 | 4.1 | 16.4 |
| IZOD Impact $\frac{1}{8}$" ft-lb/in notch | 4.3 | 0.7 ± 0.05 | 2.6 ± 1.0 | 0.82 ± 0.02 |
| UV-Stability $\Delta E_{48}$ (Sunlighter) | 3.1 | 35.2 | 23.2 | 25.01 |
| Initial | | | | |
| L | 69.7 | 85.6 | 80.7 | 81.21 |
| a | −2.0 | 0.6 | 1.6 | 1.53 |
| b | 11.0 | 13.8 | 8.7 | 7.39 |
| YI | 23.5 | 24.3 | 16.4 | 13.86 |
| Final | | | | |
| L | 68.2 | 53.6 | 67.1 | 67.57 |
| a | −2.2 | 11.5 | 6.9 | 6.69 |
| b | 13.7 | 23.8 | 26.8 | 27.70 |
| YI | 30.0 | 67.2 | 60.2 | 61.7 |

Variations of the process of this invention are within the spirit and scope of the appended claims.

What is claimed:

1. A process for preparing a product predominant in decabromodiphenylalkane and containing a minor amount of dodecabromodiphenylalkane, the process consisting essentially of: forming a stirrable reaction mass by feeding molten diphenylalkane to a reaction vessel to which aluminum halide catalyst and bromine had been previously charged, the molten diphenylalkane being maintained under a non-oxidizing atmosphere prior to the feeding, and the bromine (i) containing about 10 ppm or less impurities, and (ii) being charged in an amount which provides from about 15 to about 30 moles of bromine per mole of diphenylalkane fed; maintaining the reaction mass at a temperature in the range of from about 15° C. to about reflux during the feeding; subsequent to the feeding, separating from the reaction mass the decabromodiphenylalkane predominant product; and heat treating the separated product for a period of time ranging from 1 to 20 hours and at a temperature within the range of from about 200° C. to about 400° C. which time and temperature are sufficient to form the decabromodiphenylalkane predominant product containing the minor amount of dodecabromodiphenylalkane wherein the minor amount is less than about 20 weight percent based upon the total amount of heat-treated product thus obtained.

2. The process of claim 1 wherein the amount of bromine charged provides from about 18 to about 23 moles of bromine per mole of diphenylalkane.

3. The process of claim 1 wherein the product is separated from the reaction mass by steam stripping the reaction mass to remove non-entrained bromine therefrom.

4. The process of claim 1 wherein the product comprises 90+ weight percent decabromodiphenylalkane.

5. The process of claim 4 wherein the decabromodiphenylalkane is decabromodiphenylethane.

6. The process of claim 1 wherein the diphenylalkane reactant is 1,2-diphenylethane.

7. The process of claim 6 wherein the 1,2-diphenylethane is at a temperature of from about 55° C. to about 80° C. when fed to the reaction vessel.

8. The process of claim 7 wherein the 1,2-diphenylethane is fed under a nitrogen atmosphere.

9. A process for preparing a product predominant in decabromodiphenylethane and containing a minor amount of 1,2-dibromo-bis-pentabromophenylethane, the process consisting essentially of: forming a stirrable reaction mass by feeding molten 1,2-diphenylethane to a reaction vessel to which aluminum halide catalyst and bromine had been previously charged, the molten 1,2-diphenylethane being maintained under a non-oxidizing atmosphere prior to the feeding, and the bromine (i) containing about 10 ppm or less impurities, and (ii) being charged in an amount which provides from about 18 to about 23 moles of bromine per mole of 1,2-diphenylethane fed; maintaining the reaction mass at a temperature in the range of from about 15° C. to about reflux during the feeding; subsequent to the feeding, separating from the reaction mass the decabromodiphenylethane predominant product; and heat treating the separated product at a temperature in the range of from about 200° C. to about 280° C. for 1 to 20 hours so as to form the decabromodiphenylethane predominant product containing the minor amount of 1,2-dibromo-bis-pentabromophenylethane wherein the minor amount is less than about 20 weight percent based upon the total amount of heat-treated product thus obtained.

10. The process of claim 9 wherein the product comprises 90+ weight percent decabromodiphenylethane and at least 0.5 weight percent 1,2-dibromo-bis-pentabromophenylethane.

11. The process of claim 10 wherein, during the 1,2-diphenylethane feed the reaction mass is at a temperature within the range of from about 15° C. to about reflux.

12. The process of claim 11 wherein the product is separated from the reaction mass by steam stripping the reaction mass to remove non-entrained bromine therefrom.

* * * * *